US011707255B2

(12) United States Patent
Salgaonkar

(10) Patent No.: US 11,707,255 B2
(45) Date of Patent: Jul. 25, 2023

(54) IMAGE-BASED PROBE POSITIONING

(71) Applicant: Siemens Medical Solutions USA, Inc., Malvern, PA (US)

(72) Inventor: Vasant Salgaonkar, Sunnyvale, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 490 days.

(21) Appl. No.: 16/372,727

(22) Filed: Apr. 2, 2019

(65) Prior Publication Data
US 2020/0315572 A1    Oct. 8, 2020

(51) Int. Cl.
A61B 8/00    (2006.01)
A61B 34/20    (2016.01)
A61B 5/06    (2006.01)
A61B 8/08    (2006.01)
A61B 8/12    (2006.01)

(52) U.S. Cl.
CPC ............ *A61B 8/4245* (2013.01); *A61B 5/061* (2013.01); *A61B 8/0883* (2013.01); *A61B 8/12* (2013.01); *A61B 8/445* (2013.01); *A61B 8/463* (2013.01); *A61B 8/483* (2013.01); *A61B 34/20* (2016.02)

(58) Field of Classification Search
CPC ..... A61B 8/4245; A61B 34/20; A61B 8/0883; A61B 8/12; A61B 8/463
See application file for complete search history.

(56) References Cited

U.S. PATENT DOCUMENTS

| 8,989,842 B2 | 3/2015 | Li et al. |
| 2005/0203394 A1 | 9/2005 | Hauck |
| 2008/0287794 A1* | 11/2008 | Li ................... A61B 8/483 600/439 |
| 2010/0121190 A1 | 5/2010 | Pagoulatos et al. |
| 2010/0256558 A1* | 10/2010 | Olson .................... A61B 34/71 604/95.01 |
| 2013/0035590 A1 | 2/2013 | Ma et al. |
| 2017/0262982 A1 | 9/2017 | Pagoulatos et al. |
| 2017/0360401 A1* | 12/2017 | Rothberg ............... G06V 10/82 |
| 2018/0153437 A1* | 6/2018 | Schwartz ........... A61B 18/1492 |
| 2018/0153505 A1 | 6/2018 | Cadieu et al. |
| 2019/0355149 A1* | 11/2019 | Avendi ...................... G06T 7/74 |

(Continued)

OTHER PUBLICATIONS

Bian Ge et al: "Self-learning of inverse kinematics for feed forward control of intracardiac robotic ablation catheters", 2015 Pattern Recognition Association of South Africa and Robotics and Mechatronics International Conference (Prasa-Robmech), IEEE, Nov. 26, 2015 (Nov. 26, 2015), pp. 72-77, XP032834203 / Nov. 26, 2015.

(Continued)

*Primary Examiner* — Serkan Akar
*Assistant Examiner* — Taylor Deutsch

(57) ABSTRACT

A framework for image-based probe positioning is disclosed herein. The framework receives a current image from a probe. The current image is acquired by the probe within a structure of interest. The framework predicts a position of the probe and generates a recommendation of a next maneuver to be performed using the probe by applying the current image to a trained classifier. The framework then outputs the predicted position and the recommendation of the next maneuver.

17 Claims, 5 Drawing Sheets

(56) References Cited

U.S. PATENT DOCUMENTS

2021/0038321 A1* 2/2021 Toporek ................ A61B 34/20

OTHER PUBLICATIONS

Paul M Loschak et al: "Automated pointing of cardiac imaging catheters", 2013 IEEE International Conference on Robotics and Automation (ICRA); May 6-10, 2013; Karlsruhe, Germany, Jan. 1, 2013 (Jan. 1, 2013), pp. 5794-5799, XP055473385 / Jan. 1, 2013.
International Search Report received in corresponding International Application No. PCT/US2020/022214, dated Jun. 30, 2020.

* cited by examiner

IMAGE-BASED PROBE POSITIONING

TECHNICAL FIELD

The present disclosure generally relates to facilitating image-based positioning of a probe.

BACKGROUND

Echocardiography uses ultrasound waves to acquire images of structures inside the heart. Intracardiac echocardiogram (ICE) is a catheter-based form of echocardiography that acquires images from within the heart, rather than by gathering images of the heart by sending sound waves through the chest wall. An echocardiogram works by sending medically safe sound waves from a transducer. As the sound waves reflect back from structures in the heart to the transducer, the echocardiogram machine receives the reflected sound waves and creates a moving picture of the heart's internal structures. The echo transducer is typically located at the tip of a catheter, which is a thin, flexible tube that is inserted through a puncture into the blood vessel to the heart.

ICE users may need navigation assistance while manipulating the catheter inside the heart. ICE catheter guidance within the heart is typically established using electro-magnetic based position sensors. A third party system receives and interprets the data from these sensors to determine positions. Where sensors are not available, catheter position is often determined by a second supplemental imaging modality such as fluoroscopy. Alternatively, step-by-step guidance may be manually provided by a clinical ultrasound specialist.

However, there are various disadvantages in using such systems. For example, sensor-based guidance systems are typically more expensive and cumbersome as they typically involve a longer inflexible distal tip of the catheter, which thereby reduces maneuverability and increases chances of heart wall perforation. Additionally, the sensors may potentially interfere with nearby biomedical devices and instruments. Further, there is a higher risk of catheter manufacturing failure, along with lower yield, as well as higher material and labor cost. Fluoroscopy-based navigation systems expose physicians, patients or hospital staff to additional X-ray radiation, which may result in undesirable side effects. As for manual guidance, it requires the presence of a trained ICE sonographer, and involves additional costs associated with logistics, scheduling and procedure.

SUMMARY

Described herein is a framework for image-based probe positioning. The framework receives a current image from a probe. The current image is acquired by the probe within a structure of interest. The framework predicts a position of the probe and generates a recommendation of a next maneuver to be performed using the probe by applying the current image to a trained classifier. The framework then outputs the predicted position and the recommendation of the next maneuver.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Figure 1:
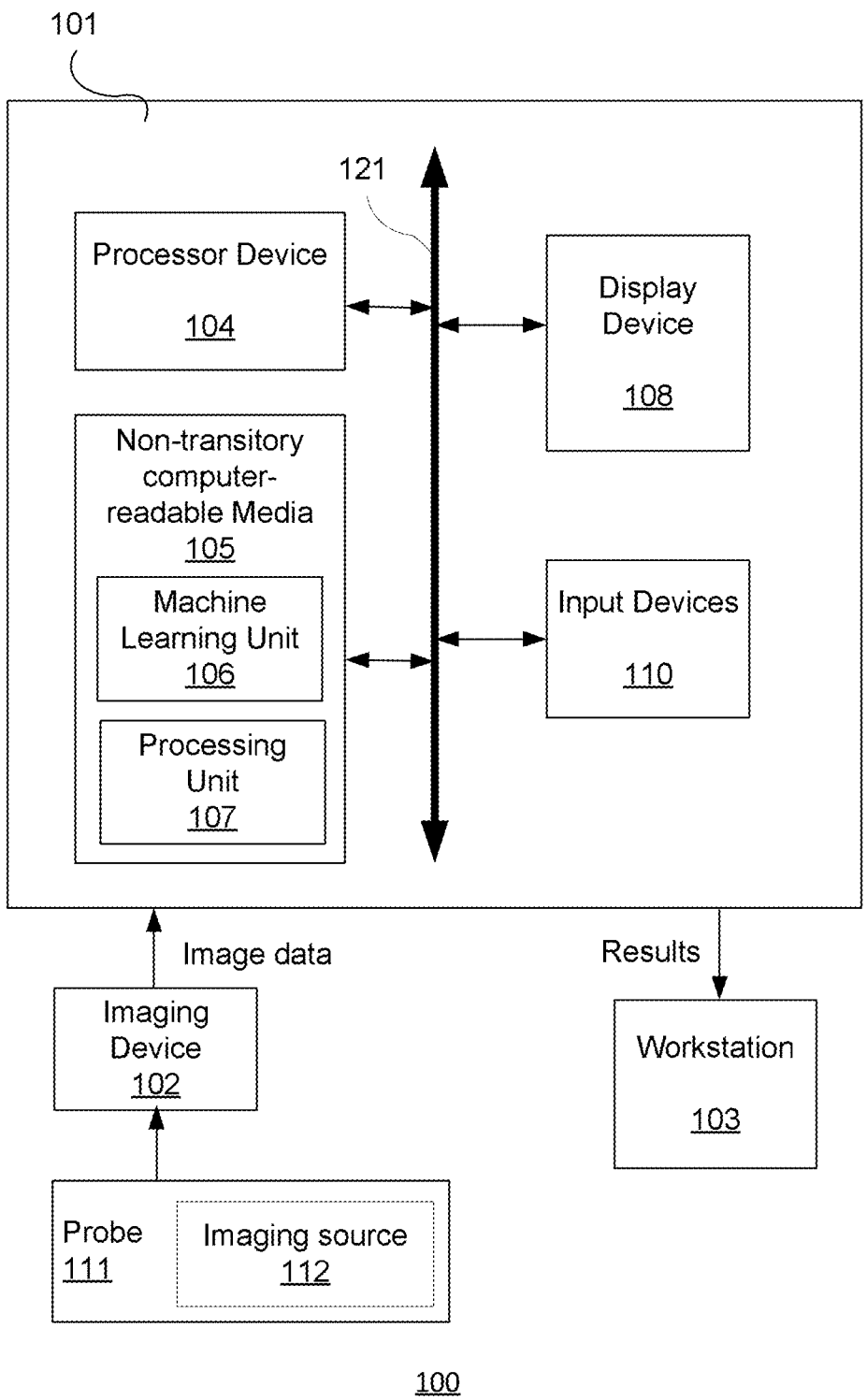
FIG. 1 is a block diagram illustrating an exemplary system.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of an interventional or therapeutic procedure, which may include times when the radiation source is either on or off. From time to time, for convenience of description, CT imaging data (e.g., cone-beam CT imaging data) may be used herein as an exemplary imaging modality. It will be appreciated, however, that data from any type of imaging modality including but not limited to x-ray radiographs, MRI, PET (positron emission tomography), PET-CT, SPECT, SPECT-CT, MR-PET, 3D ultrasound images or the like may also be used in various implementations.

Unless stated otherwise as apparent from the following discussion, it will be appreciated that terms such as "segmenting," "generating," "registering," "determining," "aligning," "positioning," "processing," "computing," "selecting," "estimating," "detecting," "tracking," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

As used herein, the term "image" refers to multi-dimensional data composed of discrete image elements (e.g., pixels for 2D images, voxels for 3D images, doxels for 4D datasets). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to $R^2$, or a mapping to $R^3$, the present methods are not limited to such images, and can be applied to images of any dimension, e.g., a 2D picture, 3D volume or 4D dataset. For a 2- or 3-Dimensional image, the domain of the image is typically a 2- or 3-Dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The terms "pixels" for picture elements, conventionally used with respect to 2D imaging and image display, "voxels" for volume image elements, often used with respect to 3D imaging, and "doxels" for 4D datasets can be used interchangeably. It should be noted that the 3D volume image is itself synthesized from image data obtained as pixels on a 2D sensor array and displays as a 2D image from some angle of view. Thus, 2D image processing and image analysis techniques can be applied to the 3D volume image data. In the description that follows, techniques described as operating upon doxels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel", "subject voxel" and "subject doxel" are used to indicate a particular image element as it is operated upon using techniques described herein.

One aspect of the present framework utilizes images input to a machine-learned classifier to predict the position (e.g., location and orientation) of a probe inside a structure of interest, such as within the heart of a patient. The predicted position may be used with a treatment or navigation protocol to generate guidance in real time for a user to, for example, steer (e.g., torque, rotate and/or translate) the probe to a desired position to visualize anatomy.

The framework relies on images acquired by the probe, and avoids the use of sensors and additional secondary imaging modalities. Positioning (or navigational) guidance generated by the present image-based framework provides several advantages. For example, ICE users can be less reliant on fluoroscopy, other on-site experts or position sensor feedback. ICE imaging is a specialized task, and many physicians are previously reluctant to use it because it is very difficult for them to precisely know the location of the catheter. Even experienced doctors can struggle with ICE positioning. They often rely on ICE sonographers or need to spend longer time navigating to standard ICE views for reorientation during a procedure. The present framework not only enables ICE users to be better informed about their device position, it may also provide step-by-step guidance to complete the procedure. Such framework can increase user confidence, facilitate user training, reduce fluoroscopy use and expand ICE adoption. In addition, by removing the use of position sensors, costs associated with using the one-time use catheters are advantageously reduced. The present framework requires no additional hardware on the ICE catheter, does not increase cost or reduce maneuverability. It also advantageously streamlines workflows, increases confidence in ICE usage, and in doing so increases ICE adoption.

It is understood that while a particular application directed to navigating an ICE catheter may be shown herein, the technology is not limited to the specific implementations illustrated. The technology may also be applied to guiding other types of probes (e.g., needle, stent, endoscope, angioplasty balloon, etc.) internal to an object or structure of interest, such as within the body of a patient.

FIG. 1 is a block diagram illustrating an exemplary system 100. The system 100 includes a computer system 101 for implementing the framework as described herein. Computer system 101 may be a desktop personal computer, a portable laptop computer, another portable device, a mini-computer, a mainframe computer, a server, a cloud infrastructure, a storage system, a dedicated digital appliance, a communication device, or another device having a storage sub-system configured to store a collection of digital data items. In some implementations, computer system 101 operates as a standalone device. In other implementations, computer system 101 may be connected (e.g., using a network) to other machines, such as imaging device 102 and workstation 103. In a networked deployment, computer system 101 may operate in the capacity of a server (e.g., thin-client server), a client user machine in server-client user network environment, or as a peer machine in a peer-to-peer (or distributed) network environment.

Computer system 101 may include a processor device or central processing unit (CPU) 104 coupled to one or more non-transitory computer-readable media 105 (e.g., computer storage or memory), a display device 108 (e.g., monitor) and various input devices 110 (e.g., mouse or keyboard) via an input-output interface 121. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein are implemented as computer-readable program code tangibly embodied in one or more non-transitory computer-readable media 105. In particular, the present techniques may be implemented by a machine learning unit 106 and a processing unit 107. Non-transitory computer-readable media 105 may further include random access memory (RAM), read-only memory (ROM), magnetic floppy disk, flash memory, and other types of memories, or a combination thereof. The computer-readable program code is executed by processor device 104 to process images or image data acquired by, for example, imaging device 102. As such, the computer system 101 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 105 may be used for storing image datasets, patient records, knowledge base, and so forth. Such data may also be stored in external storage or other memories. The external storage may be implemented using a database management system (DBMS) managed by the processor device 104 and residing on a memory, such as a hard disk, RAM, or removable media. The external storage may be implemented on one or more additional computer systems. For example, the external storage may include a data warehouse system residing on a separate computer system, a picture archiving and communication system (PACS), or any other now known or later developed hospital, medical institution, medical office, testing facility, pharmacy or other medical patient record storage system.

The probe 111 is a steerable device that is inserted into a structure of interest in an object, such as the body of a patient. For example, the probe 111 is positioned in an orifice of the patient, such as through the mouth and into the esophagus. Alternatively, the probe 111 is positioned by surgical insertion through the skin of the patient, such as for minimally invasive surgery. In other implementations, the probe 111 is inserted in an opening created as part of a surgery, such as an inter-operative probe.

The probe 111 may be an intra-operative probe, inter-cavity probe, catheter, or other medical device. In some implementations, the probe 111 is any catheter for intervention or other use within a patient. The catheter may be sized and shaped for use in the circulatory system, such as having a diameter of 10 French or less, and a length of a foot or more. Alternatively, the catheter may be sized and shaped for use at other locations in the body. The catheter is adapted for insertion within the patient, such as through a vessel or vein for extending into a heart chamber, body cavity, or other location within the patient. The catheter may include guide wires or be inserted through another previously positioned guide catheter. The catheter may include an electrode, scalpel, balloon, stent, imaging array, tube for injection, or other device for treatment of the patient.

In some implementations, the probe 111 includes an imaging source 112. The imaging source 112 is an array, sensor, lens, transducer, or other element for imaging or scanning the patient from the probe 111. For example, the imaging source 112 in the catheter is an ultrasound transducer element or array of an intracardiac echocardiography (ICE) catheter, an ultrasound transducer element of an intravascular ultrasound (IVUS) catheter, a lens or camera of an optical coherence tomography (OCT) catheter, a lens or camera of an optical imaging catheter, or is an ultrasound transducer array of a transesophageal echocardiogram (TEE) ultrasound transducer.

The imaging device 102 is external to or within the probe 111. For example, the imaging device 102 is an ultrasound system with a beamformer, detector, and/or image processor connected to the imaging source 112 but positioned externally to the patient. The external ultrasound system connects with the imaging source 112 to scan. As another example, the imaging device 102 is a camera or video device for optical imaging. The camera or video connects with the imaging source 112 to view the patient from the probe 111. In yet another example, the imaging device 102 is an optical coherence imager. In another example, the imaging device 102 is a magnetic resonance (MR) system. The MR system connects with a local coil as the imaging source 112 in the probe 111. The imaging device 102 uses the imaging source 112 to view or scan the patient from the probe 111. Alternatively, the imaging device 102 is any modality for scanning a patient from an internal or external location, such as a magnetic resonance, computed tomography, positron emission tomography, or single photon emission tomography system.

As an ultrasound transducer element or array, the imaging source 112 may be used for scanning a one, two, or three-dimensional region of a patient from the probe 111. A piezoelectric or microelectromechanical (e.g., capacitive membrane ultrasound transducer) element or elements transduce between electrical and acoustic energies for scanning the patient. An array of such elements may be used to electronically scan or steer in two or three dimensions. A single element or an array of elements may be used to mechanically scan in one or two dimensions. For example, an element or elements connect with a drive shaft and are rotated within the probe 111. The rotation causes scanning with ultrasound of different locations around the probe 111. Other arrangements may be provided.

The workstation 103 may include a computer and appropriate peripherals, such as a keyboard and display device, and can be operated in conjunction with the entire system 100. For example, the workstation 103 may communicate with the imaging device 102 so that the image data collected by the imaging device 102 can be rendered at the workstation 103 and viewed on a display device.

The workstation 103 may communicate directly with the computer system 101 to display processed image data and/or output image processing results via a graphical user interface. Alternatively, the computer system 101 itself may display processed image data and/or output image processing results via a graphical user interface on display device 108 without workstation 103. The workstation 103 may include a graphical user interface to receive user input via an input device (e.g., keyboard, mouse, touch screen, voice or video recognition interface, etc.) to manipulate visualization and/or processing of the image data. For example, the user may view the processed image data, and specify one or more view adjustments or preferences (e.g., zooming, cropping, panning, rotating, changing contrast, changing color, changing view angle, changing view depth, changing rendering or reconstruction technique, etc.).

It is to be further understood that, because some of the constituent system components and method steps depicted in the accompanying figures can be implemented in software, the actual connections between the system components (or the process steps) may differ depending upon the manner in which the present framework is programmed. Given the teachings provided herein, one of ordinary skill in the related art will be able to contemplate these and similar implementations or configurations of the present framework.

Figure 2:
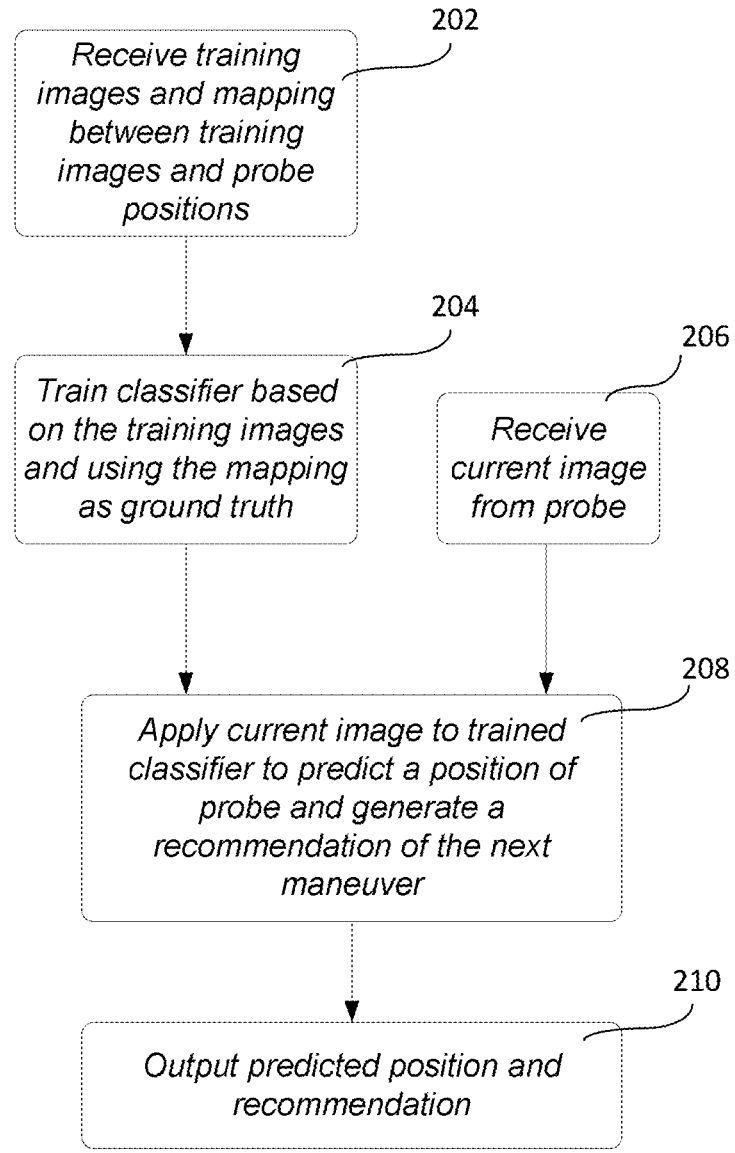
FIG. 2 shows an exemplary probe positioning method.

FIG. 2 shows an exemplary probe positioning method 200 performed by a computer system. It should be understood that the steps of the method 200 may be performed in the order shown or a different order. Additional, different, or fewer steps may also be provided. Further, the method 200 may be implemented with the system 100 of FIG. 1, a different system, or a combination thereof.

At 202, machine learning unit 106 receives training images of a structure of interest. A mapping between the training images and the respective probe positions from which the training images were acquired may also be received. The training images are acquired by a probe at particular positions within a structure of interest from different patients. The training images may be, for example, ICE images, which are ultrasound images of adjacent tissues acquired by the distal tip of steerable ICE catheters. The structure of interest is any anatomic structure identified for study. The structure of interest may be, for example, part or all of a heart or cardiac system (e.g., valve, vessel, artery, heart chamber). The training images may alternatively or additionally represent all or parts of organs, bone or other structure of interest in the patient.

Figure 3:
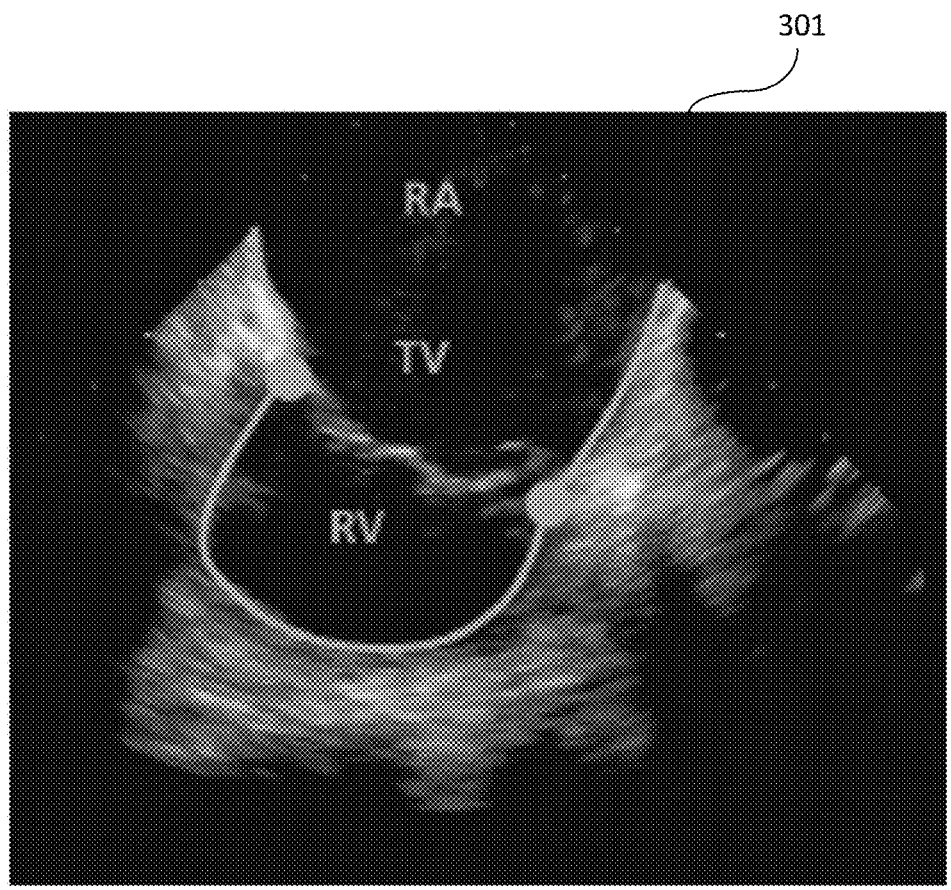
FIG. 3 shows an exemplary intracardiac echocardiogram (ICE) image.

Each training image represents locations distributed on a two-dimensional (2D) view or plane. Each view may be mapped to a relative position (e.g., location and orientation) of the probe. A view is a visualization of a predefined set of one or more anatomic landmarks. For example, the Home View may be mapped to a Home Position of the ICE catheter. The Home View may be predefined as a visualization of the right atrium (RA), right ventricle (RV) and tricuspid valve (TV) of the heart. FIG. 3 shows an exemplary ICE image 301 that represents the Home View. The Home View was acquired when the ICE catheter was positioned in the middle of the RA in an unlocked or neutral position (i.e., "Home Position"), meaning there is no steering and the tension lock is disengaged. This Home view can be used as a "basic point of navigation" from which other views can be derived.

The position of the probe may be defined relative to this Home Position, which is considered as the starting position in a typical navigation protocol. This method of navigation is similar to a human navigating a car based on street signs and landmarks instead of using a global positioning system (GPS). By rotating the ICE catheter in a clockwise direction relative to this Home position, the aortic valve, left ventricle and right ventricular outflow tracts are in the field of view before the mitral valve and left atrium (LA) with the left atrial appendage appear in the image view. With more clockwise rotation of the ICE catheter, the left superior pulmonary vein (LSPV) and left inferior pulmonary vein (LIPV) are visualized in the image view. When the ICE catheter is in a further posterior direction, the esophagus, descending aorta and right pulmonary veins (PVs) appear in the image view. The mapping between the image view and the relative position of the probe from which the image was acquired may be provided by, for example, an expert sonographer who has observed a large number of images and determined the most likely position of the probe. This expert user-derived mapping based on the multitude of images may then be utilized to train a machine learning classifier, as will be described later.

Returning to FIG. 2, at 204, machine learning unit 106 uses the training images to train a classifier to predict a relative position (e.g., location within a cardiac structure, imaging plane orientation, catheter flexion) of the probe based on an input image. The mapping between the image view and the relative position of the probe is used as ground truth for the training. In some implementations, the classifier is further trained to provide a recommendation of the next one or more maneuvers to steer the probe to the next location as required by a navigation protocol. The one or more maneuvers may be represented by navigational instructions. The navigational instructions may be displayed to guide a human user to steer (e.g., advance, pull back, rotate or flex) the probe to a particular position as required by a navigation protocol. Alternatively, the navigational instructions may be in the form of machine instructions that are executable by a robotic controller to automatically steer the probe to a desired position.

In some implementations, the classifier is further trained to correct any error in the predicted position of the probe by using a time history of position predictions. For example, consider a situation wherein the trained classifier first predicts the Home view and then predicts the next view to be a transseptal view of the left atrium (LA). This sequence of position predictions to capture views in such order is not possible. The classifier may further be trained to catch such an exception and determine the next most likely position (or view) given the time history of position predictions.

The classifier may be any one or more classifiers. A single class or binary classifier, collection of different classifiers, cascaded classifiers, hierarchal classifier, multi-class classifier, model-based classifier, classifier based on machine learning or combinations thereof may be used. Multi-class classifiers include CART, K-nearest neighbors, neural network (e.g., multi-layer perception), mixture models or others. In some implementation, the classifier is a neural network. The neural network may be, for example, a five-layer convolutional neural network (CNN). The weights of the classifier are adjusted as the training proceeds until the classifier performs adequately.

At 206, processing unit 107 receives a current image from the probe 111. The current image is acquired by the probe 111 when it is inserted into the structure of interest (e.g., cardiac system). To acquire the current image, the probe 111 may be guided and positioned in the structure of interest using steering wires and/or a previously positioned guide. The current image is the same type and for the same or similar structure of interest as the training images (e.g., ICE images of the heart).

At 208, processing unit 107 applies the current image to the trained classifier to predict a position of the probe 111 and generate a recommendation of the next one or more maneuvers to steer the probe to the next location as required by the navigation protocol. In some implementations, the robustness of the position predictions is increased by utilizing a time history of position predictions in addition to the current image to predict the position of the probe 111. The time history of position predictions is a current sequence of a predetermined number of positions that have been previously predicted by the trained classifier. The time history of position predictions may be used by the trained classifier to detect and correct any error (or exception) in the predicted position.

At 210, processing unit 107 outputs the predicted position and recommendation of the next one or more maneuvers. In some implementations, processing unit 107 displays the probe 111 at the predicted position in a graphical representation of the structure of interest. The graphical representation may be displayed via a graphical user interface at, for example, workstation 103. The graphical representation may be, for example, a catheter tip overlaid on a plane projection of a three-dimensional rendering of the structure of interest or an image-derived model of the structure of interest. The graphical representation provides a visual guide of where the probe 111 is predicted to be currently located.

In some implementations, the predicted one or more maneuvers are represented by navigational instructions to guide a human user in steering (e.g., advancing, pulling back, rotating or flexing) the probe 111 to a specific location as part of a selected treatment or navigational protocol. The navigation instructions may be displayed in a box next to (e.g., below or above) the graphical representation of the predicted position. Alternatively, the navigational instructions may be in the form of machine instructions that are executable by a robotic controller (or processor) to automatically steer the probe 111 to the desired position.

Accordingly, the probe 111 may be repositioned to a new position. A different current image may be acquired by the probe 111 at the new position. Steps 206, 208 and 210 may be repeated to update the graphical representation in substantially real time as the probe is navigated within the structure of interest and acquires new current images.

Figure 4:
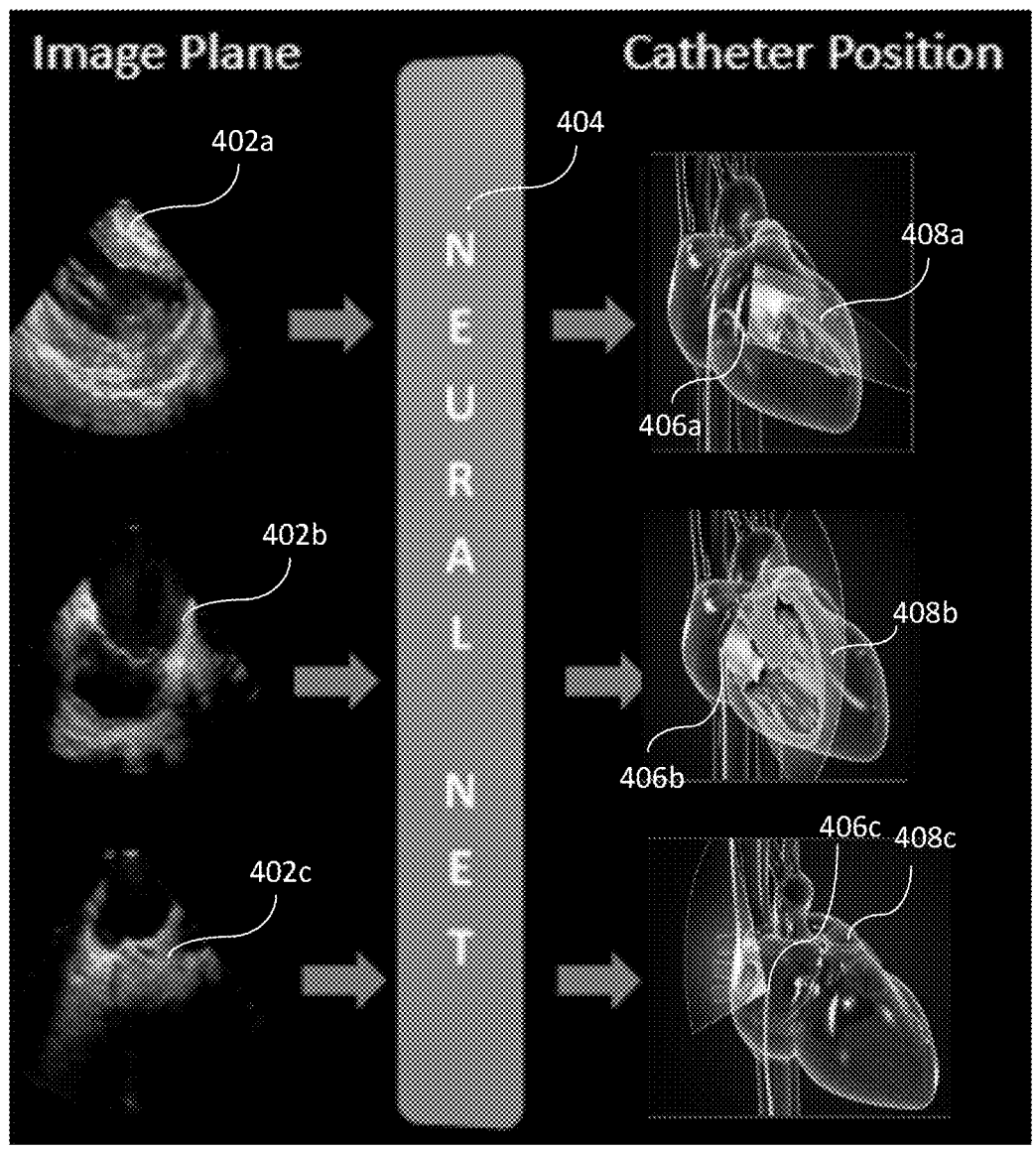
FIG. 4 illustrates exemplary input and output of the trained neural network.

FIG. 4 illustrates exemplary input and output of the trained neural network 404. The neural network 404 may be trained using the aforementioned method 200. When the trained neural network 404 receives a new ICE image 402a-c as input, it predicts the most likely position of the catheter 406a-c. The catheter 406a-c may be displayed at the predicted position within a graphical representation 408a-c of the heart on the imaging screen. The graphical representation 408a-c may be a generic 3D rendering of the heart or a computed tomography (CT) image-derived heart model of the patient. The graphical representation 408a-c may be updated in real time based on the input ICE image 402a-c, as the user navigates the catheter 406a-c within the heart.

Figure 5:
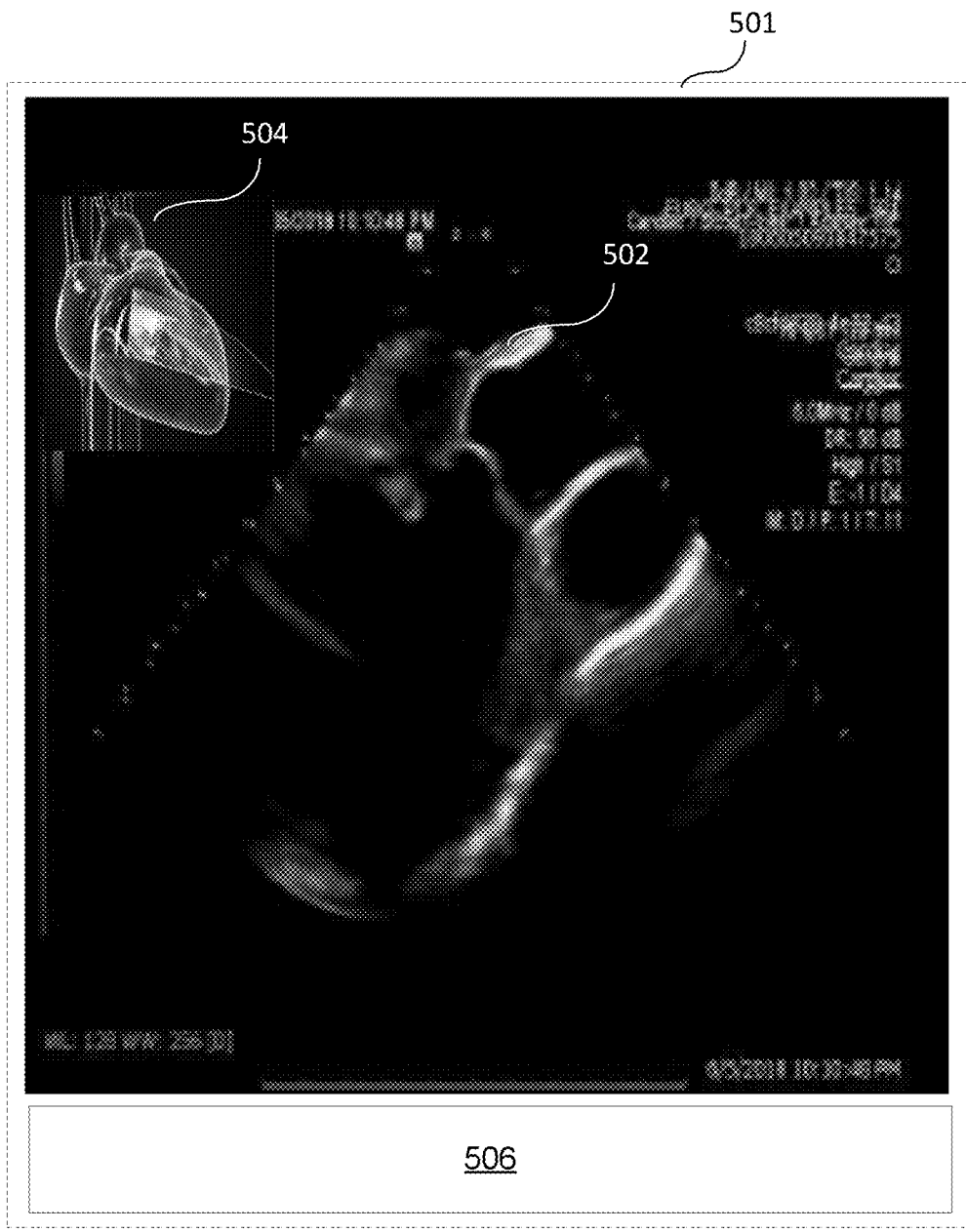
FIG. 5 shows an exemplary user interface.

FIG. 5 shows an exemplary user interface 501. The exemplary user interface 501 may be displayed at, for example, workstation 103 to guide the user in navigating an ICE catheter in the patient's heart. The user interface 501 shows a current ultrasound 2D image 502 acquired by the ICE catheter at its current position. Based on the current image 502, the classifier trained by the machine learning unit 106 predicts the most likely current position of the catheter. The catheter is displayed at the predicted position in a graphical representation 504 of the heart. The graphical representation 504 may be displayed next to the current image.

In some implementation, a box 506 is positioned below (or next) to the current image 502. The box 506 may display navigational instructions of the predicted next maneuver. The navigational instructions may be represented by, for example, text, diagram, cartoon, arrows indicating action(s) or maneuver(s) to perform, or a combination thereof. The navigational instructions may guide the user to steer and/or rotate the catheter to the next position to obtain the next view according to a navigational protocol. The graphical representation 504 and the navigational instructions in the box 506 may be updated in real time as the catheter moves and acquires new current ultrasound images 502.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. One or more non-transitory computer-readable media embodying instructions executable by machine to perform operations for intracardiac catheter positioning, comprising:
   (i) receiving a current intracardiac echocardiogram (ICE) image acquired by a catheter configured to be inserted into a heart;
   (ii) predicting a position of the catheter and generating a recommendation of a next maneuver to be performed using the catheter by applying the current ICE image and a time history of a plurality of views to a trained classifier, wherein the time history of the plurality of views comprises a current sequence of a predetermined number of the views previously generated by the trained classifier and is used by the trained classifier to detect and correct any error in the predicted position, wherein each of the plurality of views is a visualization of a predefined set of one or more anatomic landmarks and is mapped to a relative position of the catheter; and
   (iii) displaying the predicted position and the recommendation of the next maneuver;
   wherein the operations further comprise training the classifier based on a plurality of ICE training images and using a mapping between the plurality of ICE training images and a plurality of ICE catheter positions from which the plurality of ICE training images were acquired as ground truth.

2. The one or more non-transitory computer-readable media of claim 1 wherein the displaying the predicted position comprises displaying the catheter at the predicted position in a graphical representation of the heart.

3. The one or more non-transitory computer-readable media of claim 1 wherein the next maneuver is represented by navigational instructions.

4. The one or more non-transitory computer-readable media of claim 3 wherein the navigational instructions comprise machine instructions that are executable by a robotic controller to automatically steer the catheter to a desired position.

5. A method of probe positioning, comprising:
   (i) receiving a current image acquired by a probe within a structure of interest;
   (ii) predicting a position of the probe and generating a recommendation of a next maneuver to be performed using the probe by applying the current image and a time history of a plurality of views to a trained classifier, wherein the time history of the plurality of views comprises a current sequence of a predetermined number of the views previously generated by the trained classifier and is used by the trained classifier to detect and correct any error in the predicted position, wherein each of the plurality of views is a visualization of a predefined set of one or more anatomic landmarks and is mapped to a relative position of the probe; and
   (iii) displaying the predicted position and the recommendation of the next maneuvers;
   wherein the method further comprises training the classifier based on a plurality of ICE training images and using a mapping between the plurality of ICE training images and a plurality of ICE catheter positions from which the plurality of ICE training images were acquired as ground truth.

6. The method of claim 5 wherein the current image comprises an intracardiac echocardiogram (ICE) image.

7. The method of claim 5 wherein the next maneuver is represented by navigational instructions.

8. The method of claim 7 wherein the navigational instructions comprise machine instructions that are executable by a robotic controller to automatically steer the probe to a desired position.

9. The method of claim 5 wherein the displaying the predicted position comprises displaying the probe at the predicted position in a graphical representation of the structure of interest.

10. The method of claim 9 wherein the graphical representation of the structure of interest comprises a three-dimensional rendering of the structure of interest.

11. The method of claim 9 wherein the graphical representation of the structure of interest comprises an image-derived model of the structure of interest.

12. The method of claim 9 further comprising repeating steps (i), (ii) and (iii) to update the graphical representation in substantially real time as the probe acquires a new current image at a new position.

13. A system for probe positioning, comprising:
- a non-transitory memory device for storing computer readable program code; and
- a processor in communication with the non-transitory memory device, the processor being operative with the computer readable program code to perform steps including:
  (i) receiving a current image acquired by a probe within a structure of interest,
  (ii) predicting a position of the probe and generating a recommendation of a next maneuver to be performed using the probe by applying the current image and a time history of a plurality of position predictions views to a trained classifier, wherein the time history of the plurality of position predictions views comprises a current sequence of a predetermined number of the position predictions views previously generated by the trained classifier and is used by the trained classifier to detect and correct any error in the predicted position, wherein each of the plurality of views is a visualization of a predefined set of one or more anatomic landmarks and is mapped to a relative position of the probe, and
  (iii) displaying the predicted position and the recommendation of the next maneuvers;
- wherein the steps further comprise training the classifier based on a plurality of ICE training images and using a mapping between the plurality of ICE training images and a plurality of ICE catheter positions from which the plurality of ICE training images were acquired as ground truth.

14. The system of claim 13 wherein the probe comprises an intracardiac echocardiogram (ICE) catheter.

15. The system of claim 13 wherein the processor is operative with the computer readable program code to display the predicted position by displaying the probe at the predicted position in a graphical representation of the structure of interest.

16. The system of claim 15 wherein the graphical representation comprises a plane projection of a three-dimensional rendering of the structure of interest.

17. The system of claim 13 wherein the time history of the plurality of views comprises a home view, an aortic valve view, a left ventricle view, a right ventricular outflow tract view, a left atrium view, a left superior pulmonary vein view, a left inferior pulmonary vein view, an esophagus view, a right pulmonary veins view, or a combination thereof.

* * * * *